(12) United States Patent
Shirai et al.

(10) Patent No.: US 8,734,838 B2
(45) Date of Patent: May 27, 2014

(54) ADHESIVE CONTAINING POLYISOPRENE, SIS COPOLYMER, AND SOLID/LIQUID POLYISOBUTYLENE FOR EXTERNAL USE ON SKIN

(75) Inventors: Masato Shirai, Tosu (JP); Takaaki Yoshinaga, Tosu (JP); Masato Wakamatsu, Tosu (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 1333 days.

(21) Appl. No.: 10/575,562

(22) PCT Filed: Oct. 20, 2004

(86) PCT No.: PCT/JP2004/015481
§ 371 (c)(1),
(2), (4) Date: Apr. 12, 2006

(87) PCT Pub. No.: WO2005/037946
PCT Pub. Date: Apr. 28, 2005

(65) Prior Publication Data
US 2007/0077282 A1 Apr. 5, 2007

(30) Foreign Application Priority Data
Oct. 20, 2003 (JP) .................... 2003-359757

(51) Int. Cl.
*A61K 9/70* (2006.01)
*A61K 31/125* (2006.01)
*A61K 31/235* (2006.01)
*A61F 13/00* (2006.01)
*A61F 13/02* (2006.01)
*A61K 9/00* (2006.01)
*A61K 31/45* (2006.01)
*A61K 31/60* (2006.01)
*A61K 31/618* (2006.01)

(52) U.S. Cl.
CPC ............. *A61K 9/7038* (2013.01); *A61K 9/7053* (2013.01); *A61K 9/0014* (2013.01); *A61K 31/45* (2013.01); *A61K 31/60* (2013.01); *A61K 31/618* (2013.01)
USPC ........... 424/448; 424/449; 514/163; 514/692; 514/729

(58) Field of Classification Search
None
See application file for complete search history.

(56) References Cited

U.S. PATENT DOCUMENTS

| | | | | |
|---|---|---|---|---|
| 4,181,635 | A | * | 1/1980 | Takamatsu et al. ........... 524/271 |
| 4,419,480 | A | * | 12/1983 | Tabar et al. ................... 524/525 |
| 4,551,490 | A | * | 11/1985 | Doyle et al. .................... 524/22 |
| 4,855,335 | A | | 8/1989 | Neperud ....................... 523/111 |
| 5,429,591 | A | * | 7/1995 | Yamamoto et al. ............. 602/54 |
| 5,556,636 | A | * | 9/1996 | Yano et al. .................... 424/448 |
| 5,770,221 | A | * | 6/1998 | Nakamura et al. ............ 424/449 |
| 6,326,421 | B1 | * | 12/2001 | Lipman .......................... 524/22 |
| 6,451,883 | B1 | | 9/2002 | Chen et al. ...................... 524/31 |
| 6,558,792 | B1 | | 5/2003 | Vaabengaard et al. ........ 428/355 |
| 2002/0045043 | A1 | * | 4/2002 | Kuniya et al. ................. 428/343 |
| 2003/0109819 | A1 | * | 6/2003 | Tsuruda et al. ................. 602/48 |
| 2004/0243042 | A1 | * | 12/2004 | Lipman .......................... 602/43 |

FOREIGN PATENT DOCUMENTS

| | | | |
|---|---|---|---|
| EP | 1 186 644 A2 | 3/2002 | |
| EP | 1 238 664 A1 | 9/2002 | |
| EP | 1 277 466 A1 | 1/2003 | |
| GB | 1196087 | 6/1970 | |
| JP | 2002-069405 | 3/2002 | |
| JP | 2002-363069 | 12/2002 | |
| JP | 2003-063954 | 3/2003 | |
| TW | 520299 | 2/2003 | |
| WO | WO 94/11437 | 5/1994 | |
| WO | WO 00/14131 | * 3/2000 | ............ C08F 220/28 |
| WO | WO 02/064676 A2 | 8/2002 | |

OTHER PUBLICATIONS

Supplementary EPO Search Report in EP 04792647.2, Oct. 12, 2009, EPO.
Office Action and Search Report from TW Patent Application No. 93131869, Jan. 22, 2010, Taiwan.

* cited by examiner

*Primary Examiner* — Kevin S Orwig
(74) *Attorney, Agent, or Firm* — Licata & Tyrrell P.C.

(57) ABSTRACT

A pressure-sensitive adhesive composition which comprises three ingredients, i.e., polyisoprene, a styrene/isoprene/styrene copolymer, and solid polyisobutylene, in a proportion of (10-60)/(10-50)/(20-60) by weight and further contains a non-solid isobutylene polymer and a tackifier, characterized in that the amount of the non-solid isobutylene polymer is 1 to 30 pts. wt., excluding 30 pts. wt., per 100 pts. wt. of the sum of the three ingredients, i.e., the polyisoprene, styrene/isoprene/styrene copolymer, and solid polyisobutylene. When used in an adhesive patch for external use on the skin, the composition has satisfactory tackiness regardless of whether the temperature of the surrounding air is high or low, has excellent long-term storage stability, retains the necessary cohesive force, and does not unnecessarily irritate the skin.

1 Claim, No Drawings

ADHESIVE CONTAINING POLYISOPRENE, SIS COPOLYMER, AND SOLID/LIQUID POLYISOBUTYLENE FOR EXTERNAL USE ON SKIN

This patent application is the National Stage of International Application No. PCT/JP2004/015481, filed Oct. 20, 2004, which claims the benefit of priority from Japanese Application No. 2003-359757, filed Oct. 20, 2003 each of which are herein incorporated by reference in their entirety.

TECHNICAL FIELD

The invention relates to a pressure-sensitive adhesive composition and an adhesive patch for an external use on the skin using it, and more particularly relates to the adhesive patch for an external use on the skin, which includes a percutaneous absorption preparation, an emergency sticking plaster, a surgical dressing, a surgical drape, a reinforcing tape for an incision part or a taping-tape or the like.

BACKGROUND ART

A rubber pressure-sensitive adhesive agent generally consists of a rubber ingredient of a main ingredient and a tackifier, and in addition it is appropriately blended with a softener, a filler or the like. The rubber ingredient and the tackifier are hydrophobic materials which are extremely low in solubility and miscibility toward water, and an adhesive patch for an external use on the skin using such a pressure-sensitive adhesive agent easily peel off when having a bath, making a kitchen work or sweating, and therefore, it is necessary to let it have a high adhesive force in advance.

Although it is better to increase the amount of a tackifier in order to improve an adhesive force and a tack force, it lacks affinity toward water due to a high hydrophobicity as described above, and a grass transition temperature (Tg) of the system increases, resulting to a hard pressure-sensitive adhesive feeling to give a strong pain when removing, and therefore, it becomes not preferable as an adhesive patch for an external use on the skin.

In the meantime, a pressure-sensitive adhesive which contains no tackifier is proposed in patent document 1. By blending a liquid rubber in stead of a tackifier, Tg is reduced because the entire system is plasticized, whereby it is possible to improve adhesiveness toward a subject. However, there is a tendency that a cohesive force is slightly deficient, and therefore, a poor long-term stability due to deformation by flowing, a cohesion destruction, occurrence of a residue of an adhesive mass, and the like do not satisfy a use feeling as an adhesive patch for an external use on the skin.

In addition, although in patent document 2 it is proposed that three of a solid rubber ingredient at ordinary temperature, a tackifier and a liquid rubber are contained in combination at a specific ratio, more tackifier is needed to secure tackiness when the solid rubber at ordinary temperature is A-B-A type copolymer, and therefore, it gives a hard pressure-sensitive feeling and removal feeling, whereby skin irritations such as rash are easily caused. Further, when rubber solid at ordinary temperature, which does not have a physical cross-linking point, is used, a residue of an adhesive mass and the like due to an insufficient cohesive force do not satisfy a use feeling as an adhesive patch for an external use on the skin.

Patent document 1: JP, 8-506127 A
Patent document 2: JP, A, 2002-69405

DISCLOSURE OF THE INVENTION

Problem to be Solved by the Invention

Consequently, the problem to be solved by the invention is to provide a pressure-sensitive adhesive composition which has favorable tackiness regardless of whether the temperature of the surrounding air is high or low, has excellent long-term storage stability, retains the necessary cohesive force, and does not unnecessarily irritate the skin.

Means for Solving Problem

During extensive research to solve the above problems, the inventors found that, by blending polyisoprene, a styrene-isoprene-styrene copolymer, solid polyisobutylene, a non-solid polyisobutylene and a tackifier as indispensable ingredients in a specific proportion, an adhesive patch for an external use on the skin, which is excellent in a balance of the tack force and the cohesive force, excellent in a use feeling, has a removal resistance toward water and does not peel off when sweating, can be obtained, and accomplished the invention as a result of further investigation.

Namely, the invention relates to a pressure-sensitive adhesive composition which comprises three ingredients, i.e., polyisoprene, a styrene/isoprene/styrene copolymer, and solid polyisobutylene, in a proportion of (10-60)/(10-50)/(20-60) by weight and further contains a non-solid isobutylene polymer and a tackifier, characterized in that the amount of the non-solid isobutylene polymer is 1 to 30 pts. wt., excluding 30 pts. wt., per 100 pts. wt. of the sum of the three ingredients, i.e., polyisoprene, a styrene/isoprene/styrene copolymer, and solid polyisobutylene.

In addition, the invention relates to the pressure-sensitive adhesive composition, wherein the viscosity average molecular weight of the solid polyisobutylene is not less than 900,000.

Further, the invention relates to the pressure-sensitive adhesive composition, wherein the viscosity average molecular weight of the non-solid polyisobutylene is not more than 70,000.

In addition, the invention relates to the pressure-sensitive adhesive composition, wherein the blend amount of the tackifier is in a proportion of 10-80 pts. wt.

Further, the invention relates to the pressure-sensitive adhesive composition, wherein the tackifier is one or more kinds selected from a group consisting of a rosin type resin, a terpene type resin, a petroleum type resin, a phenol type resin, a xylene type resin, an alkylphenol type resin and a coumarone-indene type resin.

In addition, the invention relates to the pressure-sensitive adhesive composition, wherein it further contains a drug.

Further, the invention relates to an adhesive patch for external use on the skin, wherein the pressure-sensitive adhesive composition is laminated on a backing and covered with a liner.

The solid polyisobutylene in the invention is an elastic solid, wherein in particular preferably, the viscosity average molecular weight is not less than 900,000, and the non-solid polyisobutylene is a viscous liquid, wherein in particular preferably, the viscosity average molecular weight is not more than 70,000.

By adopting polyisoprene and solid polyisobutylene as rubber ingredients in a pressure-sensitive adhesive composition of the invention, a soft pressure-sensitive adhesive feeling and removal feeling can be obtained, while there is no uncomfortable sticky feeling and irritation to the skin is reduced. In addition, as to adjustment of the tack force, a desirable characteristics can be obtained by an appropriate blend of a low molecular polyisobutylene polymer and a tackifier. As to adjustment of the cohesive force, the cohesive force increases mainly as a styrene/isoprene/styrene copolymer increases, while it becomes soft as polyisoprene and solid polyisobutylene increase.

Effect of the Invention

A pressure-sensitive adhesive composition according to the invention is favorable in use feeling and excellent in balance between the tack force and the cohesive force, resulting to not easy peeling off when having a bath, making a kitchen work, sweating, or the like, and takes a special effect which can not be estimated by a conventional one.

BEST EMBODIMENT FOR CARRYING OUT THE INVENTION

The blend proportion of polyisoprene, a styrene/isoprene/styrene copolymer and solid isobutylene of the pressure-sensitive adhesive composition related to the invention is preferably (10-60)/(10-50)/(20-60), more preferably (15-50)/(25-45)/(30-50).

Although a preferable blend proportion of these three ingredients varies depending upon the amount of a blend ingredient except three ingredients, as a tendency, the cohesive force increases as the proportion of a styrene/isoprene/styrene copolymer is more. In addition, when polyisoprene and solid isobutylene are much in the proportion, a soft pressure-sensitive adhesive feeling and removal feeling are afforded.

As polyisoprene contained in the pressure-sensitive adhesive composition related to the invention, illustrative are IR-307 and IR-310 manufactured by Kraton Co., Ltd., IR-10 manufactured by Kurare Co., Ltd., and Nipol IR2200 manufactured by Zeon Co., Ltd.

As the styrene/isoprene/styrene copolymer contained in the pressure-sensitive adhesive composition related to the invention, illustrative are D-1107 and D-1111 manufactured by Kraton Co., Ltd., SIS5000, SIS 5002, SIS 5405, SIS 5500 and SIS 5505 manufactured by JSR Co., Ltd., Quintac 3421, Quintac 3422, Quintac 3433, Quintac 3435, Quintac 3450, Quintac 3530 and Quintac 3570 manufactured by Zeon Co., Ltd.

As the solid polyisobutylene contained in the pressure-sensitive adhesive composition related to the invention, illustrative are Vistanex MML-80, Vistanex MML-100, Vistanex MML-120 and Vistanex MML-140 manufactured by Exxon Co., Ltd.

As the non-solid isobutylene polymer contained in the pressure-sensitive adhesive composition related to the invention, illustrative are Vistanex LM-MS and Vistanex LM-MH manufactured by Exxon-Mobile Co., Ltd., Oppanol B10SFN, Oppanol B12SFN and Oppanol B13SFN manufactured by BASF Co., Ltd., Tetrax 3T, Tetrax 4T, Tetrax 5T, Tetrax 6T, Himol 4H, Himol 5H, Himol 5.5H and Himol 6H manufactured by Shin-Nihon Sekiyu Kagaku Co., Ltd., Nissan Polybutene (Polyvis) 015N, Nissan Polybutene (Polyvis) 5N, Nissan Polybutene (Polyvis) 10N and Nissan Polybutene (Polyvis) 200N manufactured by Nihonyushi Co., Ltd., Nisseki Polybutene HV-50, Nisseki Polybutene HV-300 and Nisseki Polybutene HV-1900 manufactured by Shin-Nihon Sekiyu Kagaku Co., Ltd., and one or more kinds of these can be used jointly.

The blend amount of the above non-solid isobutylene polymer is preferably 1 to 30 pts. wt., excluding 30 pts. wt., more preferably 5-25 pts. wt. Although the tack and the adhesive force incise when the blend amount is much, there is a tendency that the cohesive force is reduced.

As the tackifier contained in the pressure-sensitive adhesive composition related to the invention, rosin type resins [Estergum (Arakawa Chemical Industries), Hariester (Harima Chemicals)], terpene type resin [YS resin (Yasuhara Yushi), Piccolyte (Rika Finethec)], petroleum type resins [ARKON (Arakawa Chemical Industries), Rigalrez (Rika Finethec), Escorez (Exxon), Wingtack (Goodyear), Quintone (Zeon)], a phenol type resin, a xylene type resin, an alkylphenol type resin and a coumarone-indene type resin can be used, and one or more kinds of these can be used jointly.

The blend amount of the above tackifier is preferably 10-80 pts. wt., more preferably 30-60 30 pts. wt. Although the tack and the adhesive force increase when the blend amount is increased, it becomes unfavorable in view of a pressure-sensitive adhesive characteristics at low temperature.

The pressure-sensitive adhesive composition or the adhesive patch for external use on the skin related to the invention can be blended with a drug and further other necessary ingredient according to an aim.

A drug contained in the pressure-sensitive adhesive composition related to the invention is not particularly limited if it is a percutaneously absorbable drug, though illustrative are, for example, skin irritants, analgesic-antiinflammatory agents, antifungal agents, centrally acting drugs, diuretic agents, hypotensors, coronary vasodilators, antituissive-expectorant agents, anti-histaminic agents, anxiolytics, cardiotonic agents, contraceptives, adrenal hormones or local anesthetics.

Examples of the above skin irritant and analgesic-antiinflammatory agent include salicylic acid, glycol salicylate, acetyl salicylic acid, 1-menthol, camphor(d-, l-, dl-), peppermint oil, thymol, benzyl nicotinate, capsicum extract, capsaicin, nolic acid vanilylamide, felbinac, butyl flufenamate, piroxicam, indomethacin, ketoprofen, pranoprofen, feprazone, flurbiprofen, loxoprofen, amfenac sodium, oxaprozin, emorfazone, thiaprofen, fenbufen, pranoprofen, fentiazac, diclofenac sodium, diflunisal, ibuprofen piconol, bendazac, suprofen, buprenorphine hydrochloride, pentazocine or butorphanol tartarate.

Examples of the above antifungal agents include bifonazole, clotrimazole, tioconazole, miconazole, econazole, isoconazole, sulconazole, oxiconazole, croconazole, ketoconazole, neticonazole, riconazole, omoconazole, itraconazole, fluconazole, terbinafine, naftifine, butenafine, amorolfine, liranaftate, naphthiomate-N, tolnaftate (naphthiomate-T), tolciclate, undecylenic acid, phenyl-11-iodo-10-undecynoate, salicylic acid, siccanin, trichomycin, pyrrolnitrin, nystatin, pimaricin, griseofluvin, variotin, amphotericin B, exalamide, ciclopirox olamine, haloprogin, zinc diethyldithiocarbamate, thianthol, flucytosine, 2,4,6-tribromophenyl capranate, trimethylcetylammonium pentachlorophenate, sulfur or bark of hibisci.

Examples of the above centrally acting drugs (hypnotic-sedative agents, anti-epileptic agents, psychotropic agents) include fluphenazine, thioridazine, diazepam, chlorpromazine, nitrazepam, estazolam, triazolam, nimetazepam, flunitrazepam, haloxazolam, fluazepam, clonazepam, propericyazine, prochlorperazine, alprazolam, oxazepam, oxazolam, cloxazolam, prazepam, flutazolam, mexazolam, lorazepam, fludiazepam, bromazepam or medazepam.

Examples of the above diuretic agents include hydrothiazide, pendrofulunathiazide, ethiazide, cyclopenthiazide, hydrothiazide, penfluthizide, methyclothiazide, furosemide, metolazone, polythiazide or bendroflumethiazide.

Examples of the above hypotensors include clonidine, alseroxylon, rescinnamine, dihydroergotoxine mesilate, reserpine, prazosin, captopril, pindolol or enalapril maleate.

Examples of the above coronary vasodilators include nitroglycerin, nitroglycol, isosorbide dinitrate, papaverine hydrochloride, dipyridamole, efloxate, trimetazidine, nicorandil, cinnarizine, nairidone, molsidomine or nifedipine.

Examples of the above antituissive-expectorant agents include codeine phosphate, dihydrocodeine phosphate, ephedrine hydrochloride, clorprenaline hydrochloride, fenoterolhydrobromide, salbutamol sulfate, dimemorfan phosphate, azelastine hydrochloride, clenbuterol hydrochloride, tulobuterol hydrochloride, trimetoquinol hydrochloride, procaterol hydrochloride, bromhexine hydrochloride, trnilast, tipepidine hibezate, ketotifen fumarate, formoterol fumarate, benproperine phosphate glycyrrhetic acid.

Examples of the above antihistaminic agents include diphenhydramine hydrochloride, triprolidine hydrochloride, isotipendil hydrochloride, promethazine hydrochloride, chlorpheniramine maleate, cyproheptadine hydrochloride, clemastine fumarate, carbinoxamine maleate or dimetindene maleate.

Examples of the above annxiolytics include alprenolol, oxprenolol, bukumolol, bupranolol, pindolol, indenolol, carteolol, bufetolol, propranolol or timolol.

Examples of the above cardiotonic agents include digitalis, ubidecarenone, digoxin, methyldigoxin or deslanoside.

Examples of the above contraceptives include estradiol enantate, estradiol cypionate, levonorgestrel or estradiol.

Examples of the above adrenal hormons include hydrocortisone acetate, hydrocortisone, prednisolone, triamsinolone aceonide, dexamethasone phosphate, methylprednisolone, dichlorisone acetate, methylprednisolone acetate, fluocinolone acetonide, dexamethasone acetate, dexamethasone, fluorometholone, betamethasone phosphate sodium, betamethasone, betamethasone valarate, beclomethasone propionate, fludroxycortide, hydrocortisone butylate, betamethasone dipropionate, fluocinonide, clobetasol propionate, diflucortone valerate, halcinonide, amcinonide, prednisolone valerate or the like.

Examples of the above local anesthetics include lidocain, ethyl aminobenzoate, procaine hydrochloride, dibucaine or procaine.

The above drugs may be used blending appropriately one or more kinds.

In addition, the pressure-sensitive adhesive composition or the adhesive patch for external use on the skin of the invention can be used for an emergency sticking plaster, a surgical dressing which makes protection of the opening of a wound its purpose, a surgical drape which makes prevention of a bacterial pollution its purpose, a reinforcing tape forfix of an incision part and further a taping used when sporting.

As for other ingredients blended to the pressure-sensitive adhesive composition related to the invention, ingredients such as a softener, an absorption promoter, a resolvent, a solubilizing agent, a filler, an anti-aging agent, an antioxidant, an antiseptic, an ultraviolet absorber, a coloring agent, a flavoring agent, a surfactant or a pH adjusting agent can be blended according to a purpose of the pressure-sensitive adhesive composition.

As to the backing of the adhesive patch for external use on the skin related to the invention, for example, a film, sheet or foil of polyethylene, polypropylene, polybutadiene, ethylene-vinyl acetate copolymer, polyvinyl chloride, a polyester such as polyethylene terephthalate (PET), polybutylene terephthalate or polyethylene naphthalate, nylon, polyurethane, cotton, rayon (cellulose derivative), aluminum or the like, or a porous material or a foam material thereof, and further, an elastic or non-elastic material such as paper, woven fabric, knitted fabric or non-woven fabric are selected, and a laminate material thereof can also be used.

As to the liner of the adhesive patch for external use on the skin related to the invention, for example, a film, a sheet or a foil of polyethylene, polypropylene, a polyester such as polyethylene terephthalate (PET) or polyethylene naphthalate, nylon or aluminum, or paper or the like are selected, and a laminate material thereof can also be used. In addition, in order to make it easy to remove the pressure-sensitive adhesive agent, a surface treatment of the surface of the above liner can be made with silicone, teflon (trade mark), surfactant or the like.

Although a preparation method of the pressure-sensitive adhesive composition and the adhesive patch for external use on the skin of the invention may be a conventional method, as an example, a solubilized or kneaded pressure-sensitive adhesive composition is mixed with a drug or the like according to a purpose, directly spreaded on a backing, or spreaded on a liner such as paper or film which are once carried out with a removal treatment, followed by a pressure transfer on the backing for the preparation.

The spread thickness of a pressure-sensitive adhesive layer of the adhesive patch for external use on the skin of the invention is preferably 30 μm-400 μm, more preferably 50 μm-200 μm. It is because a release rate of a drug contained in the pressure-sensitive adhesive agent becomes bad when the thickness of the pressure-sensitive adhesive layer is thick, whereas in less than 30 μm the adhesiveness to the skin is unfavorable and there is a tendency that it becomes a cause of peeling.

EXAMPLE

In the following, the pressure-sensitive adhesive composition and the adhesive patch for external use on the skin of the invention are explained in more detail by the examples and test examples, however, the invention is not limited to these.

Example 1

To a pressure-sensitive adhesive composition consisting of polyisoprene Nipol IR2200 (manufactured by Zeon) 20 pts., solid polyisobutylene Vistanex MML-100 (manufactured by Exxon-Mobile) 40 pts., styrene/isoprene/styrene block copolymer Quintac 3570C (manufactured by Zeon) 40 pts., non-solid isobutylene polymer Vistanex LM-MH (manufactured by Exxon-Mobile) 10 pts., and ARKONP-100 (manufactured by Arakawa Chemical Industries) 40 pts. were added liquid paraffin 40 pts., zincoxide 14 pts., and hydrated silica 10 pts., and mixed. Then, the mixture was blended with methyl salicylate 6 wt. %, 1-menthol 6 wt. %, dl-camphor 1 wt. % and tocopherol acetate 2.0 wt. %, spreaded on a PET film to give the thickness of 200 μm, coated with a PET liner which was treated by silicone, and cut in a desirable shape to afford an adhesive patch for external use on the skin of the invention.

Example 2

To a pressure-sensitive adhesive composition consisting of polyisoprene Nipol IR2200 (manufactured by Zeon) 40 pts., solid polyisobutylene Vistanex MML-100 (manufactured by Exxon-Mobile) 30 pts., styrene/isoprene/styrene block copolymer Quintac 3570C (manufactured by Zeon) 30 pts., non-solid isobutylene polymer Vistanex LM-MH (manufactured by Exxon-Mobile) 10 pts., and ARKON P-100 (manufactured by Arakawa Chemical Industries) 40 pts. were added liquid paraffin 40 pts., zincoxide 14 pts., and hydrated silica 10 pts., and mixed. Then, the mixture was blended with methyl salicylate 6 wt. %, 1-menthol 6 wt. %, dl-camphor 1 wt. % and tocopherol acetate 2.0 wt. %, spreaded on a PET film to give the thickness of 200 μm, coated with a PET liner which was treated by silicone, and cut in a desirable shape to afford an adhesive patch for external use on the skin of the invention.

Example 3

To a pressure-sensitive adhesive composition consisting of polyisoprene Nipol IR2200 (manufactured by Zeon) 27 pts., solid polyisobutylene Vistanex MML-100 (manufactured by Exxon-Mobile) 55 pts., styrene/isoprene/styrene block copolymer Quintac 3570C (manufactured by Zeon) 18 pts., non-solid isobutylene polymer Vistanex LM-MH (manufactured by Exxon-Mobile) 5 pts., and ARKON P-100 (manufactured by Arakawa Chemical Industries) 60 pts. were added liquid paraffin 60 pts., zinc oxide 14 pts., and hydrated silica 10 pts., and mixed. Then, the mixture was blended with methyl salicylate 6 wt. %, 1-menthol 6 wt. %, dl-camphor 1 wt. % and tocopherol acetate 2.0 wt. %, spreaded on a PET film to give the thickness of 200 μm, coated with a PET liner which was treated by silicone, and cut in a desirable shape to afford an adhesive patch for external use on the skin of the invention.

Example 4

To a pressure-sensitive adhesive composition consisting of polyisoprene Nipol IR2200 (manufactured by Zeon) 27 pts., solid polyisobutylene Vistanex MML-100 (manufactured by Exxon-Mobile) 55 pts., styrene/isoprene/styrene block copolymer Quintac 3570C (manufactured by Zeon) 18 pts., non-solid isobutylene polymer Vistanex LM-MH (manufactured by Exxon-Mobile) 15 pts., and ARKON P-100 (manufactured by Arakawa Chemical Industries) 60 pts. were added liquid paraffin 60 pts., zinc oxide 14 pts., and hydrated silica 10 pts., and mixed. Then, the mixture was blended with methyl salicylate 6 wt. %, 1-menthol 6 wt. %, dl-camphor 1 wt. % and tocopherol acetate 2.0 wt. %, spreaded on a PET film to give the thickness of 200 μm, coated with a PET liner which was treated by silicone, and cut in a desirable shape to afford an adhesive patch for external use on the skin of the invention.

Example 5

To a pressure-sensitive adhesive composition consisting of polyisoprene Nipol IR2200 (manufactured by Zeon) 27 pts., solid polyisobutylene Vistanex MML-100 (manufactured by Exxon-Mobile) 55 pts., styrene/isoprene/styrene block copolymer Quintac 3570C (manufactured by Zeon) 18 pts., non-solid isobutylene polymer Vistanex LM-MH (manufactured by Exxon-Mobile) 25 pts., and ARKON P-100 (manufactured by Arakawa Chemical Industries) 60 pts. were added liquid paraffin 60 pts., zinc oxide 14 pts., and hydrated silica 10 pts., and mixed. Then, the mixture was blended with methyl salicylate 6 wt. %, 1-menthol 6 wt. %, dl-camphor 1 wt. % and tocopherol acetate 2.0 wt. %, spreaded on a PET film to give the thickness of 200 μm, coated with a PET liner which was treated by silicone, and cut in a desirable shape to afford an adhesive patch for external use on the skin of the invention.

Example 6

To a pressure-sensitive adhesive composition consisting of polyisoprene Nipol IR2200 (manufactured by Zeon) 50 pts., solid polyisobutylene Vistanex MML-100 (manufactured by Exxon-Mobile) 30 pts., styrene/isoprene/styrene block copolymer Quintac 3570C (manufactured by Zeon) 20 pts., non-solid isobutylene polymer Nisseki Polybutene HV-300 (manufactured by Shin-Nihon Sekiyu Kagaku) 10 pts., and ARKON P-100 (manufactured by Arakawa Chemical Industries) 40 pts. were added liquid paraffin 40 pts., zinc oxide 14 pts., and hydrated silica 10 pts., and mixed. Then, the mixture was blended with methyl salicylate 6 wt. %, 1-menthol 6 wt. %, dl-camphor 1 wt. % and tocopherol acetate 2.0 wt. %, spreaded on a PET film to give the thickness of 200 μm, coated with a PET liner which was treated by silicone, and cut in a desirable shape to afford an adhesive patch for external use on the skin of the invention.

Example 7

To a pressure-sensitive adhesive composition consisting of polyisoprene Nipol IR2200 (manufactured by Zeon) 50 pts., solid polyisobutylene Vistanex MML-100 (manufactured by Exxon-Mobile) 30 pts., styrene/isoprene/styrene block copolymer Quintac 3570C (manufactured by Zeon) 20 pts., non-solid isobutylene polymer Nisseki Polybutene HV-300 (manufactured by Shin-Nihon Sekiyu Kagaku) 20 pts., and ARKON P-100 (manufactured by Arakawa Chemical Industries) 40 pts. were added liquid paraffin 40 pts., zinc oxide 14 pts., and hydrated silica 10 pts., and mixed. Then, the mixture was blended with methyl salicylate 6 wt. %, 1-menthol 6 wt. %, dl-camphor 1 wt. % and tocopherol acetate 2.0 wt. %, spreaded on a PET film to give the thickness of 200 μm, coated with a PET liner which was treated by silicone, and cut in a desirable shape to afford an adhesive patch for external use on the skin of the invention.

Example 8

To a pressure-sensitive adhesive composition consisting of polyisoprene Nipol IR2200 (manufactured by Zeon) 50 pts., solid polyisobutylene Vistanex MML-100 (manufactured by Exxon-Mobile) 30 pts., styrene/isoprene/styrene block copolymer Quintac 3570C (manufactured by Zeon) 20 pts., non-solid isobutylene polymer Vistanex LM-MH (manufactured by Exxon-Mobile) 10 pts., and ARKON P-100 (manufactured by Arakawa Chemical Industries) 40 pts. were added liquid paraffin 40 pts., zinc oxide 14 pts., and hydrated silica 10 pts., and mixed. Then, the mixture was blended with methyl salicylate 6 wt. %, 1-menthol 6 wt. %, dl-camphor 1 wt. % and tocopherol acetate 2.0 wt. %, spreaded on a PET film to give the thickness of 200 μm, coated with a PET liner which was treated by silicone, and cut in a desirable shape to afford an adhesive patch for external use on the skin of the invention.

Example 9

To a pressure-sensitive adhesive composition consisting of polyisoprene Nipol IR2200 (manufactured by Zeon) 50 pts., solid polyisobutylene Vistanex MML-100 (manufactured by Exxon-Mobile) 30 pts., styrene/isoprene/styrene block copolymer Quintac 3570C (manufactured by Zeon) 20 pts., non-solid isobutylene polymer Vistanex LM-MH (manufactured by Exxon-Mobile) 20 pts., and ARKON P-100 (manufactured by Arakawa Chemical Industries) 40 pts. were added liquid paraffin 40 pts., zinc oxide 14 pts., and hydrated silica 10 pts., and mixed. Then, the mixture was blended with methyl salicylate 6 wt. %, 1-menthol 6 wt. %, dl-camphor 1 wt. % and tocopherol acetate 2.0 wt. %, spreaded on a PET film to give the thickness of 200 μm, coated with a PET liner which was treated by silicone, and cut in a desirable shape to afford an adhesive patch for external use on the skin of the invention.

Example 10

To a pressure-sensitive adhesive composition consisting of polyisoprene Nipol IR2200 (manufactured by Zeon) 21 pts., solid polyisobutylene Vistanex MML-100 (manufactured by Exxon-Mobile) 43 pts., styrene/isoprene/styrene block copolymer Quintac 3570C (manufactured by Zeon) 36 pts., non-solid isobutylene polymer Vistanex LM-MH (manufactured by Exxon-Mobile) 15 pts., and ARKON P-100 (manufactured by Arakawa Chemical Industries) 60 pts. were added liquid paraffin 70 pts., zinc oxide 14 pts., and hydrated silica 10 pts., and mixed. Then, the mixture was blended with methyl salicylate 6 wt. %, 1-menthol 6 wt. %, dl-camphor 1 wt. % and tocopherol acetate 2.0 wt. %, spreaded on a PET film to give the thickness of 200 μm, coated with a PET liner which was treated by silicone, and cut in a desirable shape to afford an adhesive patch for external use on the skin of the invention.

Example 11

To a pressure-sensitive adhesive composition consisting of polyisoprene Nipol IR2200 (manufactured by Zeon) 21 pts., solid polyisobutylene Vistanex MML-100 (manufactured by Exxon-Mobile) 43 pts., styrene/isoprene/styrene block copolymer Quintac 3570C (manufactured by Zeon) 36 pts., non-solid isobutylene polymer Nisseki Polybutene HV-300 (manufactured by Shin-Nihon Sekiyu Kagaku) 7.5 pts., and ARKON P-100 (manufactured by Arakawa Chemical Industries) 60 pts. were added liquid paraffin 70 pts., zinc oxide 14 pts., and hydrated silica 10 pts., and mixed. Then, the mixture was blended with methyl salicylate 6 wt. %, 1-menthol 6 wt. %, dl-camphor 1 wt. % and tocopherol acetate 2.0 wt. %, spreaded on a PET film to give the thickness of 200 μm, coated with a PET liner which was treated by silicone, and cut in a desirable shape to afford an adhesive patch for external use on the skin of the invention.

Example 12

To a pressure-sensitive adhesive composition consisting of polyisoprene Nipol IR2200 (manufactured by Zeon) 21 pts., solid polyisobutylene Vistanex MML-100 (manufactured by Exxon-Mobile) 43 pts., styrene/isoprene/styrene block copolymer Quintac 3570C (manufactured by Zeon) 36 pts., non-solid isobutylene polymer Nisseki Polybutene HV-300 (manufactured by Shin-Nihon Sekiyu Kagaku) 15 pts., and ARKON P-100 (manufactured by Arakawa Chemical Industries) 60 pts. were added liquid paraffin 70 pts., zinc oxide 14 pts., and hydrated silica 10 pts., and mixed. Then, the mixture was blended with methyl salicylate 6 wt. %, 1-menthol 6 wt. %, dl-camphor 1 wt. % and tocopherol acetate 2.0 wt. %, spreaded on a PET film to give the thickness of 200 μm, coated with a PET liner which was treated by silicone, and cut in a desirable shape to afford an adhesive patch for external use on the skin of the invention.

Comparative Example 1

To a pressure-sensitive adhesive composition consisting of solid polyisobutylene Vistanex MML-100 (manufactured by Exxon-Mobile) 30 pts., styrene/isoprene/styrene block copolymer Quintac 3570C (manufactured by Zeon) 30 pts., and ARKON P-100 (manufactured by Arakawa Chemical Industries) 40 pts. were added liquid paraffin 40 pts., zinc oxide 14 pts., and hydrated silica 10 pts., and mixed. Then, the mixture was blended with methyl salicylate 6 wt. %, 1-menthol 6 wt. %, dl-camphor 1 wt. % and tocopherol acetate 2.0 wt. %, spreaded on a PET film to give the thickness of 200 μm, coated with a PET liner which was treated by silicone, and cut in a desirable shape to afford an adhesive patch for external use on the skin of the comparative example 1.

Comparative Example 2

To a pressure-sensitive adhesive composition consisting of polyisoprene Nipol IR2200 (manufactured by Zeon) 27 pts., solid polyisobutylene Vistanex MML-100 (manufactured by Exxon-Mobile) 55 pts., styrene/isoprene/styrene block copolymer Quintac 3570C (manufactured by Zeon) 18 pts., and ARKON P-100 (manufactured by Arakawa Chemical Industries) 60 pts. were added liquid paraffin 60 pts., zinc oxide 14 pts., and hydrated silica 10 pts., and mixed. Then, the mixture was blended with methyl salicylate 6 wt. %, 1-menthol 6 wt. %, dl-camphor 1 wt. % and tocopherol acetate 2.0 wt. %, spreaded on a PET film to give the thickness of 200 μm, coated with a PET liner which was treated by silicone, and cut in a desirable shape to afford an adhesive patch for external use on the skin of the comparative example 2.

Comparative Example 3

To a pressure-sensitive adhesive composition consisting of polyisoprene Nipol IR2200 (manufactured by Zeon) 50 pts., solid polyisobutylene Vistanex MML-100 (manufactured by Exxon-Mobile) 30 pts., styrene/isoprene/styrene block copolymer Quintac 3570C (manufactured by Zeon) 20 pts., and ARKON P-100 (manufactured by Arakawa Chemical Industries) 40 pts. were added liquid paraffin 40 pts., zinc oxide 14 pts., and hydrated silica 10 pts., and mixed. Then, the mixture was blended with methyl salicylate 6 wt. %, 1-menthol 6 wt. %, dl-camphor 1 wt. % and tocopherol acetate 2.0 wt. %, spreaded on a PET film to give the thickness of 200 μm, coated with a PET liner which was treated by silicone, and cut in a desirable shape to afford an adhesive patch for external use on the skin of the comparative example 3.

Comparative Example 4

To a pressure-sensitive adhesive composition consisting of polyisoprene Nipol IR2200 (manufactured by Zeon) 21 pts., solid polyisobutylene Vistanex MML-100 (manufactured by Exxon-Mobile) 43 pts., styrene/isoprene/styrene block copolymer Quintac 3570C (manufactured by Zeon) 36 pts., and ARKON P-100 (manufactured by Arakawa Chemical Industries) 60 pts. were added liquid paraffin 70 pts., zinc oxide 14 pts., and hydrated silica 10 pts., and mixed. Then, the mixture was blended with methyl salicylate 6 wt. %, 1-menthol 6 wt. %, dl-camphor 1 wt. % and tocopherol acetate 2.0 wt. %, spreaded on a PET film to give the thickness of 200 μm, coated with a PET liner which was treated by silicone, and cut in a desirable shape to afford an adhesive patch for external use on the skin of the comparative example 4.

As to the adhesive patches for external use on the skin, which were obtained the above examples and the comparative examples, the finger tack, the 180° removal value and the probe tack value were evaluated by the following methods and the results were shown in Table.

[Finger Tack]

A tack strength of a pressure-sensitive adhesive agent as well as an adhesive strength, a remaining skin stickiness and the like were evaluated from a tactile sensation when touching the pressure-sensitive adhesive agent, a feeling when removing and a skin feeling after it, and the like (⊚=favorable, ○=acceptable, △=just about acceptable, X=unacceptable). Further, as to one having a pressure-sensitive adhesive feeling of special note, its characteristics were described (Table 1).

[Probe Tack]

The measurement was made according to the test method described in ASTDM2979 (peeling rate 10 mm/sec, adhesion time 2 sec).

[180° Removal]

The measurement was made according to the test method described in JIS Z0237 (sample width 20 mm, removal rate 300 mm/min, on condition that the adhered material is Bakelite).

TABLE 1

Table 1

| | Probe tack (gf) | 180° removal (gf) | | Finger tack |
|---|---|---|---|---|
| Example 1 | 32.6 | 29.3 | ○ | Favorable |
| Example 2 | 23.3 | 25.2 | ○ | Favorable |
| Example 3 | 38.5 | 73.8 | ○ | Slightlybadbite |
| Example 4 | 46.4 | 70.9 | ⊚ | Very favorable |
| Example 5 | 69.6 | 85.5 | ○ | Favorable |
| Example 6 | 43.2 | 28.1 | ⊚ | Very favorable |
| Example 7 | 57.7 | 37.4 | ⊚ | Very favorable |
| Example 8 | 53.3 | 37.9 | ○ | Favorable |
| Example 9 | 77.2 | 50.3 | ○ | Favorable |
| Comparative example 1 | 40.1 | 55.4 | △ | Hard adhesive mass, accompanying a pain |
| Comparative example 2 | 35.7 | 39.0 | △ | Weak tackiness |
| Comparative example 3 | 36.2 | 29.3 | △ | Weak tackiness |

Generally, it is considered that the probe tack value of an adhesive patch for external use on the skin is in the range of 20-150 gf and the 180° removal is 20-200 gf, while the adhesive patches for external use on the skin of the invention are in this acceptable range both for the probe tack value and the 180° removal and apparently have an enough tackiness. Further, in the finger tack test, the tackiness and the use feeling were both excellent.

In the meantime, as to the adhesive patches for external use on the skin of the comparative examples 1, 2 and 3, they have seemingly enough tackiness in the probe tack and 180° removal tests, however, the tackiness and the use feeling when actually applying to the skin are inferior to those of the adhesive patches for external use on the skin of the invention.

Test Example 2

Stickiness Test When Sweating

Each adhesive patch of the examples 10, 11 and 12 related to the invention and the comparative example 4 was stuck to 6 subjects, and the stickiness was evaluated when the subjects sweated.

The subjects were stuck with each adhesive patch at the inner side of the forearm. They ate, continued going up and down of stairs for 5 minutes and walked for 15 minutes in a room maintained at 30° C., and recorded the results in a questionnaire.

TABLE 2

Table 2

| | Results (Stickiness) |
|---|---|
| Example 10 | ○ |
| Example 11 | ⊚ |
| Example 12 | ○ |
| Comparative example 4 | X |

⊚ = favorable,
○ = acceptable,
X = unacceptable

Test Example 3

Stickiness Test When Having a Bath

Each adhesive patch of the examples 10, 11 and 12 related to the invention and the comparative example 4 was stuck to 6 subjects, and the stickiness was evaluated when the subjects had a bath.

The subjects were stuck with each adhesive patch at the inner side of the forearm. After 1 hour they had a bath, soaked in the bathtub for 5 minutes, and then recorded the results in a questionnaire.

TABLE 3

Table 2

| | Results (Stickiness) |
|---|---|
| Example 10 | ○ |
| Example 11 | ⊚ |
| Example 12 | ⊚ |
| Comparative example 4 | X |

⊚ = favorable,
○ = acceptable,
X = unacceptable

As is evident from the above test results, the pressure-sensitive adhesive composition and the adhesive patch for external use on the skin of the invention are excellent in a balance of the adhesive force and the cohesive force, are favorable in a use feeling, have an anti-sweating property when sweating, and therefore, are extremely wide in a range of applicability.

INDUSTRIAL APPLICABILITY

Since the adhesive patch for external use on the skin of the invention is excellent in a balance of the tack force and the cohesive force, it can be utilized for an adhesive patch for external use on the skin such as a percutaneous absorption preparation by containing an ingredient such as a drug, and greatly contributes to development of related industries.

The invention claimed is:

1. A percutaneous absorption preparation which comprises:
   (a) one or more analgesic-antiinflammatory agents selected from the group consisting of methyl salicylate, L-menthol and dl-camphor,
   (b) polyisoprene,
   (c) a styrene/isoprene/styrene copolymer, and
   (d) solid polyisobutylene,
   wherein the preparation comprises (b), (c) and (d) in a proportion of (27-50)/(18-20)/(30-55) parts by weight respectively and 100 parts by weight in total relative to the total weight of (b), (c) and (d) and further contains a non-solid isobutylene polymer and a tackifier; wherein the amount of the non-solid isobutylene polymer is 10-20 parts by weight per 100 parts by weight relative to the total weight of (b), (c) and (d); and wherein the content of the tackifier is in a proportion of 40-60 parts by weight relative to the total weight of (b), (c) and (d), thereby exhibiting a removal resistance to water.

* * * * *